(12) United States Patent
Tanghoj et al.

(10) Patent No.: US 7,682,353 B2
(45) Date of Patent: Mar. 23, 2010

(54) CATHETER DEVICE

(75) Inventors: Allan Tanghoj, Kokkedal (DK); Lars Bogelund Jensen, Rodovre (DK)

(73) Assignee: Coloplast A/S, Humlebaek (DK)

( * ) Notice: Subject to any disclaimer, the term of this patent is extended or adjusted under 35 U.S.C. 154(b) by 288 days.

(21) Appl. No.: 10/722,574

(22) Filed: Nov. 28, 2003

(65) Prior Publication Data

US 2004/0158231 A1    Aug. 12, 2004

Related U.S. Application Data

(63) Continuation-in-part of application No. 09/893,514, filed on Jun. 29, 2001, now abandoned, and a continuation-in-part of application No. 10/026,819, filed on Dec. 27, 2001, now Pat. No. 7,311,698, and a continuation-in-part of application No. 10/184,081, filed on Jun. 28, 2002.

(30) Foreign Application Priority Data

| Jun. 29, 2001 | (DK) | 2001 01041 |
| Sep. 24, 2001 | (DK) | 2001 01386 |
| Dec. 13, 2001 | (DK) | 2001 01869 |
| Dec. 13, 2001 | (DK) | 2001 01870 |
| Apr. 17, 2002 | (DK) | 2002 00569 |
| Apr. 17, 2002 | (DK) | 2002 00570 |
| Jun. 13, 2002 | (DK) | 2002 00895 |

(51) Int. Cl.
*A61M 27/00* (2006.01)
*A61M 5/32* (2006.01)
*A61F 5/44* (2006.01)

(52) U.S. Cl. ............ 604/544; 604/349; 604/163
(58) Field of Classification Search ........... 604/544, 604/39–42, 363, 523, 264–5, 171–2, 327–331, 604/349–350
See application file for complete search history.

(56) References Cited

U.S. PATENT DOCUMENTS 2,856,932 A    10/1958    Griffitts (Continued)

FOREIGN PATENT DOCUMENTS

CN    2168601 Y    6/1994

(Continued)

OTHER PUBLICATIONS

LoFric—Patientenratgeber—1996.

(Continued)

*Primary Examiner*—Kevin C Sirmons
*Assistant Examiner*—Andrew M Gilbert
(74) *Attorney, Agent, or Firm*—Daniel G. Chapik

(57) ABSTRACT

A kit for preparing a medical catheter from catheter sections comprises a tubular protective member surrounding a first, proximal one of the catheter sections. The kit further comprises a joint for interconnecting the catheter sections, the joint defining a substantially liquid tight seal at one end of a substantially annular and longitudinally extending cavity provided between the proximal end portion of the first catheter section and an inner wall of the tubular protective member. Following removal of the tubular protective member, one of the catheter sections is exposed and ready for insertion into the urethra.

11 Claims, 13 Drawing Sheets

U.S. PATENT DOCUMENTS

| | | | |
|---|---|---|---|
| 3,186,410 A | 6/1965 | Buono | |
| 3,335,723 A * | 8/1967 | Waldman, Jr. | 604/163 |
| 3,537,451 A | 11/1970 | Beck et al. | |
| 3,648,704 A | 3/1972 | Jackson | |
| 3,661,153 A | 5/1972 | Polk et al. | |
| 3,750,875 A * | 8/1973 | Juster | 206/364 |
| 3,769,981 A | 11/1973 | McWhorter | |
| 3,853,130 A | 12/1974 | Sheridan | |
| 3,854,483 A * | 12/1974 | Powers | 604/172 |
| 3,865,666 A | 2/1975 | Shoney | |
| 3,867,945 A | 2/1975 | Long | |
| 3,894,540 A | 7/1975 | Bonner, Jr. | |
| 3,898,993 A * | 8/1975 | Taniguchi | 604/172 |
| 3,901,965 A | 8/1975 | Honeyman, III | |
| 3,934,721 A * | 1/1976 | Juster et al. | 206/364 |
| 4,041,122 A | 8/1977 | Quick et al. | |
| 4,043,345 A | 8/1977 | Kramann et al. | |
| 4,188,954 A | 2/1980 | Patel et al. | |
| 4,204,527 A | 5/1980 | Wu et al. | |
| 4,246,909 A | 1/1981 | Wu et al. | |
| 4,284,459 A | 8/1981 | Patel et al. | |
| 4,363,406 A | 12/1982 | Salvadori | |
| 4,421,509 A | 12/1983 | Schneider et al. | |
| 4,511,358 A | 4/1985 | Johnson et al. | |
| 4,551,292 A | 11/1985 | Fletcher et al. | |
| 4,583,967 A | 4/1986 | Harris | |
| 4,588,160 A | 5/1986 | Flynn et al. | |
| 4,615,472 A | 10/1986 | Nash | |
| 4,673,161 A | 6/1987 | Flynn et al. | |
| 4,743,236 A | 5/1988 | Manschot | |
| 4,750,877 A | 6/1988 | McFarlane | |
| 4,802,650 A | 2/1989 | Stricker | |
| 4,811,847 A * | 3/1989 | Reif et al. | 206/571 |
| 4,850,350 A | 7/1989 | Jackson | |
| 5,035,399 A | 7/1991 | Rantanen-Lee | |
| 5,041,085 A | 8/1991 | Osborne et al. | |
| 5,147,341 A | 9/1992 | Starke et al. | |
| 5,167,646 A | 12/1992 | Swafford | |
| 5,167,647 A | 12/1992 | Wijkamp et al. | |
| RE34,223 E | 4/1993 | Bonaldo | |
| 5,242,398 A | 9/1993 | Knoll et al. | |
| 5,320,613 A | 6/1994 | Houge et al. | |
| 5,354,263 A | 10/1994 | Coll | |
| 5,391,155 A | 2/1995 | Sachse | |
| 5,409,469 A | 4/1995 | Schaerf | |
| 5,454,798 A | 10/1995 | Kubalak et al. | |
| 5,510,065 A | 4/1996 | McFarlane | |
| 5,531,717 A * | 7/1996 | Roberto et al. | 604/271 |
| 5,643,236 A | 7/1997 | Hadley | |
| 5,653,700 A * | 8/1997 | Byrne et al. | 604/329 |
| 5,690,645 A | 11/1997 | Van Erp | |
| 5,745,926 A | 5/1998 | Cailleteau | |
| 5,756,144 A | 5/1998 | Wolff et al. | |
| 5,863,287 A * | 1/1999 | Segawa | 600/121 |
| 5,951,929 A | 9/1999 | Wilson | |
| 6,004,305 A | 12/1999 | Hursman et al. | |
| 6,053,905 A | 4/2000 | Daignault, Jr. et al. | |
| 6,059,107 A | 5/2000 | Nosted et al. | |
| 6,063,063 A | 5/2000 | Harboe et al. | |
| 6,090,075 A | 7/2000 | House | |
| 6,149,996 A | 11/2000 | Helgerson et al. | |
| 6,158,912 A | 12/2000 | Miraglia et al. | |
| 6,355,004 B1 * | 3/2002 | Pedersen et al. | 600/581 |
| 6,409,717 B1 | 6/2002 | Israelsson et al. | |
| 6,524,926 B1 | 2/2003 | Allman et al. | |
| 6,578,709 B1 | 6/2003 | Kavanagh et al. | |
| 6,602,244 B2 | 8/2003 | Kavanagh et al. | |
| 6,634,498 B2 * | 10/2003 | Kayerød et al. | 206/364 |
| 6,786,884 B1 | 9/2004 | DeCant et al. | |
| 7,311,698 B2 | 12/2007 | Tanghøj et al. | |
| 2002/0103467 A1 | 8/2002 | Kubalak | |
| 2003/0018293 A1 | 1/2003 | Tanghoj et al. | |
| 2003/0018322 A1 | 1/2003 | Tanghoj et al. | |
| 2004/0153051 A1 | 8/2004 | Israelsson et al. | |
| 2004/0158231 A1 | 8/2004 | Tanghoj et al. | |
| 2004/0163980 A1 | 8/2004 | Tanghoj et al. | |
| 2004/0236293 A1 | 11/2004 | Tanghoj et al. | |
| 2004/0254562 A1 | 12/2004 | Tanghoj et al. | |
| 2005/0043715 A1* | 2/2005 | Nestenborg et al. | 604/544 |
| 2006/0025753 A1* | 2/2006 | Kubalak et al. | 604/544 |

FOREIGN PATENT DOCUMENTS

| | | |
|---|---|---|
| DE | 24 62 537 | 6/1977 |
| DE | 28 01 851 | 9/1981 |
| DE | 38 16 906 A1 | 11/1989 |
| DE | 4140099 | 5/1993 |
| DE | 198 26 746 | 11/1999 |
| DE | 201 03 653 | 9/2002 |
| DK | 172941 | 10/1999 |
| DK | 173714 | 7/2001 |
| EP | 0 206 558 A1 | 12/1986 |
| EP | 0336984 | 12/1990 |
| EP | 0 471 429 B1 | 2/1992 |
| EP | 0 495 263 | 7/1992 |
| EP | 0 658 488 | 6/1995 |
| EP | 0 807 447 | 11/1997 |
| EP | 0824930 | 2/1998 |
| EP | 0 570 370 | 6/1998 |
| EP | 0925802 | 6/1999 |
| EP | 0958911 | 11/1999 |
| EP | 0 959 930 | 12/1999 |
| EP | 1 023 882 | 8/2000 |
| EP | 1 034 811 A1 | 9/2000 |
| EP | 0923398 | 11/2001 |
| EP | 0923390 | 4/2003 |
| EP | 1 406 690 | 4/2004 |
| EP | 1 116 567 B1 | 3/2006 |
| FR | 2293948 | 7/1976 |
| GB | 1 482 873 | 8/1977 |
| GB | 1 493 257 | 11/1977 |
| GB | 1493257 | 11/1977 |
| GB | 1 524 704 | 9/1978 |
| GB | 1 598 843 | 9/1981 |
| GB | 2 193 485 | 2/1988 |
| GB | 2 230 702 A | 10/1990 |
| GB | 2231801 | 11/1990 |
| GB | 2 278 285 | 8/1997 |
| GB | 2 336 830 | 11/1999 |
| HU | 187 406 | 12/1987 |
| HU | 189 812 | 8/1988 |
| HU | 263 A | 4/1994 |
| HU | 210 728 B | 7/1995 |
| HU | 213 805 B | 10/1997 |
| HU | 215 792 B | 3/1999 |
| HU | P9903763 | 3/2000 |
| HU | 217 867 B | 4/2000 |
| HU | 219 423 B | 4/2001 |
| HU | 219 512 B | 4/2001 |
| HU | 220 326 B | 12/2001 |
| HU | P0201498 | 9/2002 |
| HU | 222 366 B1 | 6/2003 |
| HU | 223 145 B1 | 3/2004 |
| JP | 51-35585 | 3/1976 |
| JP | 62-57352 | 4/1980 |
| JP | 62-186155 | 2/1990 |
| JP | 4-218168 | 8/1992 |
| JP | 7-501232 | 2/1995 |
| JP | 11-347129 | 12/1999 |
| SE | 518 002 | 8/2002 |
| WO | 89/02763 | 4/1989 |
| WO | 90/00960 | 2/1990 |
| WO | 91/18640 | 12/1991 |
| WO | WO 91/18640 | 12/1991 |

| | | |
|---|---|---|
| WO | 92/07607 | 5/1992 |
| WO | 92/13718 | 8/1992 |
| WO | 92/18310 | 10/1992 |
| WO | WO 92/18310 | 10/1992 |
| WO | WO 93/01855 | 2/1993 |
| WO | 93/04723 | 3/1993 |
| WO | WO 93/04723 | 3/1993 |
| WO | 93/19717 | 10/1993 |
| WO | 94/08653 | 4/1994 |
| WO | WO 94/08653 | 4/1994 |
| WO | 95/24235 | 9/1995 |
| WO | WO 95/24235 | 9/1995 |
| WO | 96/19254 | 6/1996 |
| WO | WO 96/19254 | 6/1996 |
| WO | 97/07707 | 3/1997 |
| WO | WO 97/07707 | 3/1997 |
| WO | 97/26937 | 7/1997 |
| WO | WO 97/26937 | 7/1997 |
| WO | 97/47349 | 12/1997 |
| WO | WO 97/47349 | 12/1997 |
| WO | 98/06642 | 2/1998 |
| WO | 98/11932 | 3/1998 |
| WO | 98/58988 | 12/1998 |
| WO | 98/58989 | 12/1998 |
| WO | 98/58990 | 12/1998 |
| WO | 99/23978 | 5/1999 |
| WO | 99/30761 | 6/1999 |
| WO | WO 99/42155 | 8/1999 |
| WO | 00/16843 | 3/2000 |
| WO | WO 00/16843 | 3/2000 |
| WO | 00/30575 | 6/2000 |
| WO | WO 00/30575 * | 6/2000 |
| WO | WO 01/32240 | 5/2001 |
| WO | 03/008029 | 1/2003 |

OTHER PUBLICATIONS

LoFric—Hinweise zum katherisieren mit LoFric—1996.

* cited by examiner

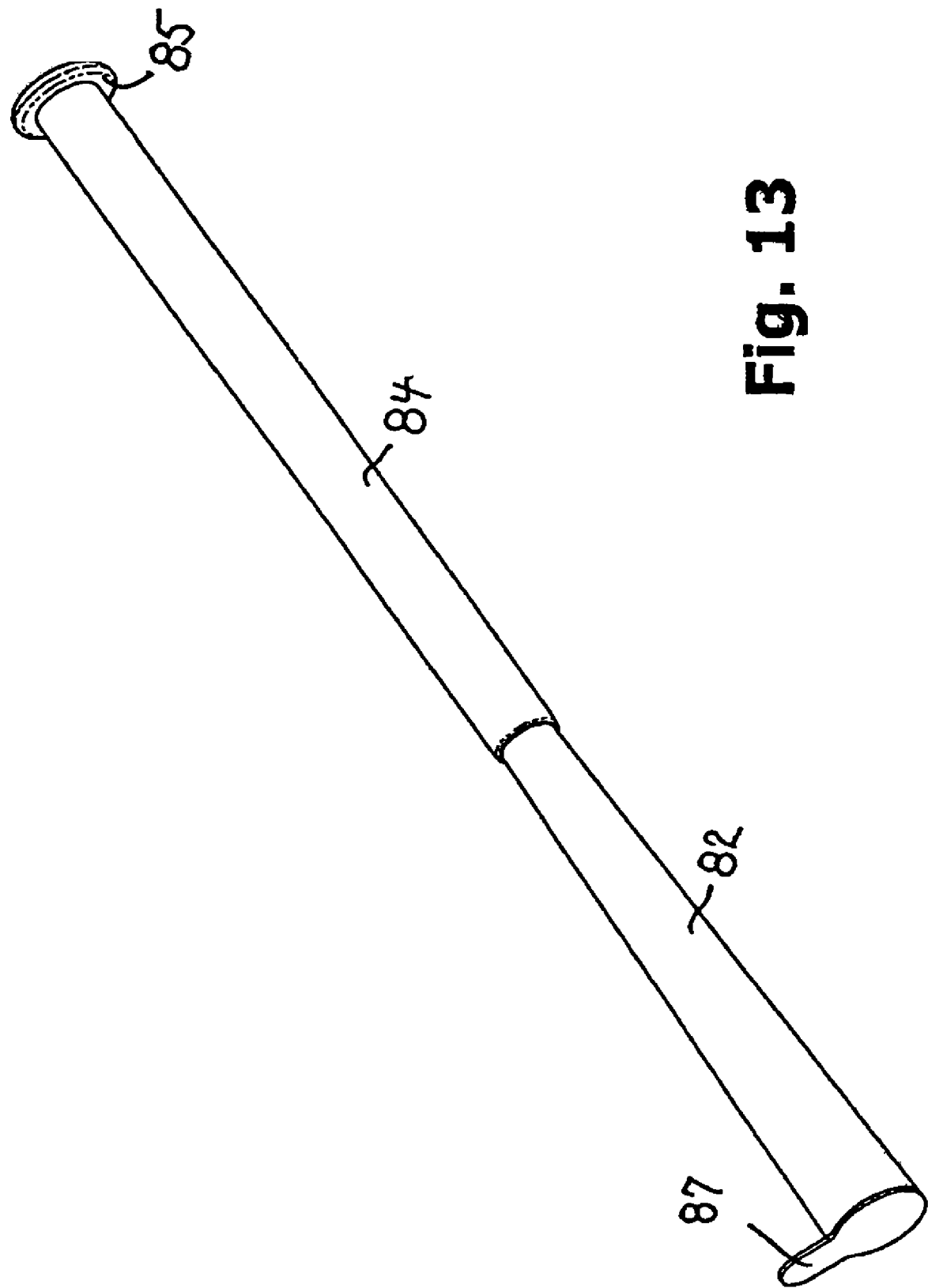

CATHETER DEVICE

This is a Continuation-in-Part of U.S. Ser. No. 09/893,514 filed Jun. 29, 2001, now abandoned, and a Continuation-in-Part of U.S. Ser. No. 10/026,819, filed on Dec. 27, 2001, now U.S. Pat. No. 7,311,698, and a Continuation-in-Part of U.S. Ser. No. 10/184,081, filed on Jun. 28, 2002, in which applications are hereby incorporated by reference.

FIELD OF THE INVENTION

The present invention relates to an elongated tubular catheter member for draining bodily fluids, e.g. from the bladder.

BACKGROUND OF THE INVENTION

Catheters for draining the bladder are increasingly used for intermittent as well as indwelling or permanent catheterisation. Typically catheters are used by patients suffering from urinary incontinence or by disabled individuals like para- or tetraplegics who may have no control permitting voluntary urination and for whom catheterisation may be the way of urinating.

Catheterisation is thus increasingly becoming a daily-life procedure significantly improving quality of life for a large group of patients.

Typically, catheters are designed for one-time use and accordingly the costs for producing, packing and sterilising a catheter is an important issue. Existing catheters are made from a single piece of a continuous catheter tube. Typically, the thickness of the catheter tube is constant throughout its length.

The length of the catheter enables insertion of a certain length into the urethra until urine starts to flow. At this point, a certain over-length of the catheter should be available. The over-length supports for the user to firmly hold the catheter and to guide the urine to a place of disposal and to withdraw the catheter safely and without any risk of the catheter disappearing into the urethra.

Existing catheters are designed to minimise the risk of sores in the mucous membrane and to give substantially no sensation of pain during insertion. Accordingly known catheters are typically provided with a smooth and slippery surface optimised for safe and comfortable insertion into the urethra. Therefore, it may often be difficult, not least for the disabled user, to handle the catheter by manipulation of the slippery over-length.

It is often important that the tubular member does not collapse or kink and thereby blocks the passage for the urine to drain through the catheter. Existing catheters are therefore typically made from a form stabile and relatively hard but still bendable tube e.g. made from PVC, PU or PE. Since the hardness of the tubes is selected relatively high with the view to avoid kinking, the catheters may collapse if they are bend with a too small radius of curvature.

Accordingly, existing catheters not only have a considerable length but they are also typically packed in an elongate condition. Therefore the existing catheters may be troublesome to handle and to bring along, not least for the individuals for whom catheterisation is a daily-life procedure, wherein catheterisation takes place several times a day and wherein the used catheters must be disposed via the garbage collection.

DESCRIPTION OF THE INVENTION

It is an object of preferred embodiments of the present invention to overcome the above described disadvantages of the known catheters.

Accordingly, the invention provides a kit for preparing a catheter for draining a human bladder, the kit comprising at least two catheter sections defining a longitudinally extending passage therein, the sections being arranged in a coextending fashion with a tubular protective member surrounding a first, proximal one of said catheter sections, the kit further comprising a joint for interconnecting the first and the second catheter section, the joint defining a substantially liquid tight seal at a distal end of a substantially annular and longitudinally extending cavity provided between the proximal end portion of the first catheter section and an inner wall of the tubular protective member, the tubular protective member being removably connected to the joint and/or to the second catheter section, so that, when the tubular protective member is removed, a proximal end portion of the first catheter section is exposed and ready for insertion into the human urethra.

In particular, the catheter may be provided so that the sections are adapted to be moved between at least two positions with respect to each other. One position being a position wherein the second section surrounds the first section and the other position being a position wherein the second section forms an extension for the first section.

The joint between the first section and the second section may be a telescopical joint providing a liquid tight seal between the sections while the they are moved between the first position and the second position. As an example, the first section may be provided with a piston seal adapted to slide along the inner surface of the second section while the first section is being pulled out of second section between the first and second position.

In order to allow the user to insert the first section into a body canal, a locking arrangement of may be provided for locking the position of the first section with respect to the second section, when the sections are in the second position, i.e. when the catheter is in a configuration ready for insertion into the body canal.

In order to allow the user to pull the first catheter section out of the second catheter section without touching the insertable part of the catheter, the tubular protective member may preferably be provided to engage the first catheter section in a locking engagement. Thereby, it will be allowed to use the tubular protective member to pull the first catheter section out of the second catheter section.

When the first catheter section has been pulled out of the first catheter section, i.e. when the sections are in the second position, i.e. in the position wherein the second catheter section forms an extension for the first catheter section, the tubular protective member should be allowed to disengage the first catheter section. When the tubular protective member has been removed, the catheter is in a "ready to insert" state.

In order to use the second catheter section as a sealing envelope or package for the first catheter section, i.e. for the insertable catheter section, the distal end of the first catheter section may preferably be adapted to seal an opening in a distal end of the second catheter section while the sections are in the first position and not to seal set opening when the sections are in the second position. When the sections are brought into the second position, i.e. when the catheter is "ready for insertion", the opening in the distal end of the second section may be used for draining the bodily liquids, e.g. urine out of the catheter.

In order to allow the annular cavity to be used e.g. for carrying a frictional reducing substance, e.g. a water or saline solution for a hydrophilic catheter, a hydrogel or similar lubricating substance, the kit may preferably be provided with a sealing engagement between the tubular protective member and the first catheter section when the tubular protective member is engaging the first catheter section. When the tubular protective member is disengaged from the first catheter section, i.e. after the catheter has reached its "ready for insertion state", the annular cavity is open to the ambient atmosphere thus exposing the insertable tip of the first catheter section and allowing the user to drain surplus friction reducing substances.

In one embodiment, the first catheter section is provided with a hydrophilic surface and the friction reducing substance provided in the annular cavity is a liquid swelling medium, e.g. water or a saline solution.

The catheter sections could be provided in the form of oblong tubular, hollow sections wherein the passage is defined inside the sections or the sections may comprise an oblong solid kernel with one or more vanes extending radially from the kernel and along the entire length thereof. The vanes thus defines a number of draining passages for draining urine between the kernel and a bodily draining passage, e.g. the urethra. The advantage of using a passage defined between a solid kernel and a wall of the urethra is that the flow of bodily fluid cleans the urethra and thus reduces the risk of infection compared with a traditional catheter, wherein the bodily fluid is drained inside the catheter isolated from the body canal.

A rigidity of substantially the full length of the catheter allows for manipulation of the catheter as one uniform catheter tube. Thereby, insertion of the proximal end of the catheter may be performed without touching the part of the catheter which is going to be inserted into the urethra. Preferably the catheter is provided with a bending moment defined as the product between E-modulus and moment of inertia of at least 1 $MPamm^4$.

Since the proximal (inserted) end of the catheter, for male individuals, must pass prostate in a curved passage, the proximal end portion of the catheter, e.g. the first 10-50 mm., such as 20-40 mm., such as 25-35 mm., such as the first 30 mm. of the catheter may be provided with an even lower bending moment defined as the product between E-modulus and moment of inertia of less than e.g. 0.6 $MPamm^4$ or even less than 0.3 $MPamm^4$. Other parts of the catheter, e.g. a distal end portion where the urine is drained into the lavatory, a bag or similar place of disposal, may similarly be provided with a reduced bending moment.

The cross-sectional flow area or the hydraulic radius defined as the ratio of the cross-sectional flow area to the wetted perimeter, may be selected independently upon the length, e.g. on the basis of the size of the urethra, which size depends on the individual using the catheter. Each of the sections may have either the same cross-sectional flow area or hydraulic radius or each section may have individual cross-sectional flow areas or hydraulic radiuses. However, at least one part of one section should have a cross-sectional shape and size adapted for the size of urethra or an artificial urinary canal. Similarly one section should preferably have a length selected on the basis of the length of the urethra or the urinary canal. Thereby it may be achieved that only one section is to be inserted and therefore no transition between sections needs to be inserted. However, especially for male individuals where urethra is particularly long, a catheter having an inserted length divided in two sections or more may be provided. In this specific case it will be appropriate to provide a transition between the sections which at least on the outer surface of the catheter have substantially no recess or sharp edge.

At least one of the catheter sections may be provided in a length in the range of 50-90 mm, such as in the range of 55-85 mm, such as in the range of 60-80 mm, such as with a length in the size of 70 mm, which length has been found to be a suitable insertable length for most female individuals. For male individuals, catheter sections may be provided in a length in the range of 180-250 mm, such as in the range of 190-240 mm, such as in the range of 200-230 mm such as in the size of 220 mm. For the male individuals it may further be preferred to provide at least a part of the inserted end of the catheter in a material or in dimensions so that a the tube becomes very flexible, without kinking. This will ease the passage of the catheter past prostate.

The outer cross-sectional shape of at least one of the sections should preferably be substantially circular with a cross-sectional area in the range of 0.5 $mm^2$-30 $mm^2$.

Even more preferred is to provide at least one of the sections with a hydraulic radius ("cross-sectional area"/"circumferential length") in the size of 0.2-1.5 mm. Alternatively, at least one of the sections should have a cross-sectional shape matching the shape of urethra or an artificial urinary canal, still with a cross-sectional area in the range of 0.5 $mm^2$-30 $mm^2$. or a hydraulic radius in the size of 0.2-1.5 mm. However, the other of the sections does not necessarily have to have the same cross-sectional shape, nor the same hydraulic radius. The wall thickness of the catheter should preferably be in the range between 0.5-1.5 mm.

The catheter or at least a part of the catheter could be made from a thermoplastic elatomeric material, other thermoplastic materials, curable elastomeric materials, polyamide resins or elastomers or any mixture thereof, i.e. the group may comprise materials like, PVC, PU, PE, latex, and/or Kraton™.

In one embodiment, the catheter may be divided in separate catheter sections. Each catheter section has at least one end provided with means for connecting the section with another section corresponding to an adjacent part of the catheter. As an example the catheter may be divided into two tubular connectable pieces connected by connecting means.

Preferably, the connecting means are provided with a rigidity allowing for manipulation of at least one of the catheter sections by manipulation of one of the other catheter sections. At least the connection between each of the pieces should provide sufficient rigidity to allow one proximal section to be inserted into the urethra by manipulation of one of the other sections. Therefore, the connection is preferably provided so that at least the part of the catheter extending the connection zone, has a bending moment defined as the product between E-modulus and moment of inertia of at least 0.6 $MPamm^4$ such as at least 1 $MPamm^4$. In order not to have the individual sections falling apart during use, the connection should preferably be adapted to take up an axial force of at least 0.5 Newton or at least to take up an axial force larger than the axial force required for withdrawal of the catheter from the urethra or artificial urinary canal.

The pieces may be connected e.g. telescopically or via a hinge enabling one of two sections to rotate in relation to the other of the two sections. It is appreciated that the sections are in fixed engagement so that they do not disconnect during use of the catheter, while urine is drained through the catheter. However, since the urine is always drained in one direction, the connection does not necessarily have to be liquid-tight. As an example a telescopic connection may be established by inserting the section adapted for insertion into urethra into a distal section. The flow direction of the urine will at least substantially prevent the connection from leaking even though the connection as such is not completely liquid tight. However, a completely sealed connection may provide an even safer catheter with a reduced risk of contaminating hands etc.

In one embodiment wherein the two catheter sections are arranged in a telescopic fashion, the first catheter section may be intended for insertion into the human urethra, whereas the second catheter section is usually intended for forming a prolongation of the catheter outside the human urethra during use of the catheter. In use, that is in the second mutual configuration of the two catheter sections, the second catheter section preferably coextends with the first catheter section away from a distal end of the first catheter section. In the first mutual configuration, which usually is the configuration in which the telescopic kit is stored and transported, at least a portion of the first catheter section may be surrounded by the second catheter section. In the first mutual configuration, the tubular protective member is provided between an outer surface of the first catheter section and an inner wall of the second catheter section. The dimensions of the tubular protective member and the catheter sections may be such that, in the second mutual configuration, a substantially annular and longitudinally extending cavity is formed between an outer surface of the first catheter section and an inner wall of the second catheter section. The first catheter section may have a hydrophilic surface, and a liquid swelling medium may be provided in the annular cavity, so as to swell the hydrophilic surface of the first catheter section, whereby the first catheter section being encapsulated in the tightly sealed annular cavity may be preserved in its wet, swelled condition for a period of 1-5 years, such as 3-5 years, or more. A tight sealing of the annular cavity is desired for all kinds of catheter surfaces, including hydrophilic and hydrophobic catheter surfaces, in order to prevent contamination to enter into the cavity. Thus, in the first mutual condition, the telescopical joint may serve to define a liquid and contamination tight seal between the second catheter section and an ambient atmosphere.

A distal end of the second catheter section is preferably provided with a tight seal which may be tight to both liquids and contamination, and which may be removable, so that when a distal end of the second catheter section is inserted into, e.g., a urine collection bag, a passage for urine is formed at the location from which the seal has been removed. The tubular protective member is preferably removable when the first and second catheter sections are in the second mutual position, so that, when the tubular protective member is removed, the proximal end portion of the first catheter section is exposed and ready for insertion into the human urethra. The distal end of the second catheter section may as an alternative be provided into one piece with a collection bag. As an example, the second catheter section may be provided with a plastic welding-flange for adhesively bonding a plastic collection bag to the second catheter section.

According to another preferred embodiment, the catheter may comprise at least two sections not being separated but being divided by a bendable zone. The bendable zone could e.g. be a bellow shaped section or the zone could be an area wherein the thickness of the tubular material is smaller and wherein the zone accordingly has a lower bending moment. The zone could e.g. be provided in a more resilient or flexible material allowing for bending the catheter tube without kinking or damaging the tube.

In general, the problems of introducing a catheter into urethra depend not only of the size of the introduced part of the catheter but also on the slipperiness of the introduced part. The catheter section or at least a part of the catheter section or sections adapted for insertion into urethra or an artificial urinary canal may provide a surface slipperiness for easy and safe insertion. However, it has been found that lubricated or slippery surfaces, are difficult to handle, not least for a user having reduced dexterity. It is therefore an object of the present invention to provide a catheter with an inserted part being treated so as to provide a slippery is surface and another part not being treated, so as to provide a surface which may easily be handled. The division of the catheter into one part being treated and one part not being treated may preferably follow the aforementioned division of the catheter with the purpose of making the catheter collapsible or separable. According to an alternative embodiment, the parts may be provided in the form of one part being smooth and another part being provided with a rough surface.

According to a preferred embodiment, at least one of the sections is provided with gripping means easing a firm grip in the catheter. Not least for the disabled user, the gripping means will improve the value of the catheter considerably. Gripping means may be provided as a radially extending flange or flanges or as a zone having a large outer cross sectional diameter. The catheter, or at least one of the catheter sections, may also be provided with means for engaging an external handle. As an example, one of the tubular catheter tubes may be provided with a ring-shaped bulge for attaching a handle. The ring-shaped bulge could be provided as a short tubular piece of plastic with a larger radial size than the catheter, the catheter being inserted and glued into the short piece of plastic.

A section provided with a hydrophilic surface treated with a liquid swelling medium may provide an excellent lubrication for the insertion and also provide compatibility with the body tissue. It is therefore a further preferred embodiment of the invention to provide at least one of the sections with a hydrophilic surface layer.

One of the catheter sections could be used as a sterile package for the other sections, e.g. by arranging the sections in a telescopic manner inside one section, closing and sealing that section in both ends, e.g. by a peelable and optionally a metallised foil e.g. made from a thermoplastic elatomeric material, other thermoplastic materials, curable elastomeric materials, polyamide resins or elastomers or any mixture thereof, i.e. the group may comprise materials like, PVC, PU, PE, latex, and/or Kraton™, thereby allowing for sterilising the assembly by radiation.

The liquid swelling medium for the hydrophilic surface may be provided in the package for initiation of the low friction character already when the catheter is being packed. The liquid swelling medium may simply be a saline solution, a bactericidal solution capable of swelling the hydrophilic surface and capable of keeping the surface in a sterile condition or it may be pure water. The swelling may also be initiated already before packaging of the catheter, the catheter then being packed in a substantially gas impermeable package for conservation of the moistened surface. Furthermore, the liquid swelling medium may be provided in a capsule or container packed together with the catheter for swelling of the hydrophilic material immediately prior to the insertion.

With the catheter there may be provided a supporting member for being introduced into a first conduit of the catheter, the conduit being for draining urine, the supporting member being provided with an outer cross-sectional shape and radial size substantially equal to the inner cross-sectional shape and size of the elongate tube so as to support said tube against collapsing during bending of the tube, the supporting member having a flexibility allowing curling.

The flexible elongated tube could have the shape of a regular catheter of the known kind. Preferably, the tube or at least a part of the tube is made from a thermoplastic elatomeric material, other thermoplastic materials, curable elastomeric materials, polyamide resins or elastomers or any mixture thereof, i.e. the group may comprise materials like, PVC, PU, PE, latex, and/or Kraton™.

The supporting member supports the catheter to avoid collapsing when the catheter is bend, e.g. for the purpose of packing the catheter in user friendly short packages. The supporting member may be either solid or the supporting member may be hollow and thus defining a second conduit. The solid supporting member should be adapted for removal prior to draining of the bladder, whereas a hollow supporting member may remain inside the tube while the bladder is emptied through the first and second conduit.

The supporting member may as an example be glued inside the elongated tube or the supporting member may even be moulded into the tube during the process of producing the tube. The supporting member may even be completely integrated in the elongated tube. The supporting member could be made from any suitable material such as e.g. plastic, steel, aluminium, a thermoplastic elatomeric material, other thermoplastic materials, curable elastomeric materials, polyamide resins or elastomers or any mixture thereof. As an example, the supporting member may be a helical spring provided in a length in the range of 20-60 mm, such as in the range of 30-50 mm., such as in the range of 35-45 mm. The spring should be positioned inside the elongated tube in the zone where it is desired to bend the catheter, e.g. midway along the longitudinal axis of the elongated tube. During use, the urine is drained through the first conduit of the elongated tube and past the supporting member through the second conduit.

In one embodiment, the supporting member is provided in a length in the range of 60-120 mm, such as in the range of 70-110 mm., such as in the range of 80-100 mm. and the supporting member may even be extending out of the discharge end of the elongated tube. This will enable the user to remove the supporting member during the process of inserting the catheter into urethra.

The supporting member may be provided with gripping means for easing withdrawal of the supporting member from the discharge end during insertion of the catheter.

A method for producing a urinary catheter comprising a proximal insertion section defining an inner elongated passage for urine, and at least one opening near a proximal end of the proximal insertion section for allowing urine to pass from the human bladder into the inner elongated passage, may comprise the steps of:

providing a mould, defining the shape of at least the proximal insertion section,
forming the proximal insertion section by injection moulding,
removing the proximal insertion section from the mould.

Whereas longitudinally extending catheters made from plastics materials have hitherto been manufactured by a relatively costly process involving extruding the catheter body, forming a rounded tip thereof by heat treatment, cutting transversely extending passages for urine near the tip of the catheter by means of a cutting tool, and rounding edges of the transversely extending passages by heat treatment, the method according to the fourth aspect of the invention has the advantage that it allows for a more efficient and more accurate controllable manufacturing process with less waste of material and fewer production steps.

The catheter may further comprise a connector part for connecting the proximal insertion section to a further catheter section or to a urinary collection bag. The connector part may be made from the same material as the proximal insertion section, whereby, at the step of forming the proximal insertion section, the proximal insertion section and the connector part may be formed substantially simultaneously. Alternatively, the connector part may be made from a material different from the material of the proximal insertion section, whereby the connector part and the proximal insertion section are formed in distinct process steps, for example in a multi-component injection moulding process.

BRIEF DESCRIPTION OF THE DRAWINGS

Preferred embodiments of the invention will now be described in details with reference to the drawing in which:

FIGS. 12 and 13 show yet a further embodiment, wherein the catheter sections are arranged in a coextending fashion.

DETAILED DESCRIPTION OF THE DRAWINGS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
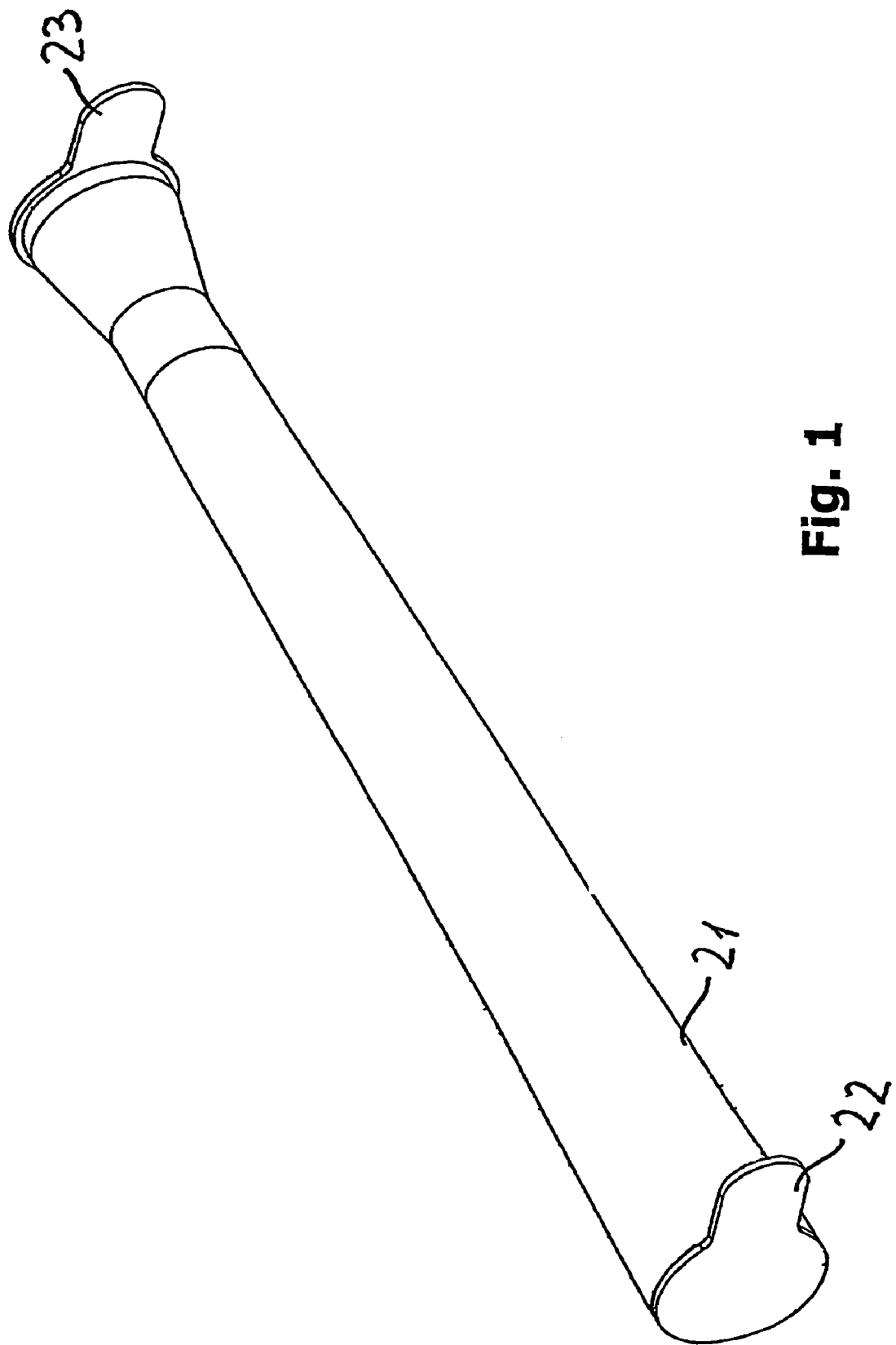
FIG. 1 shows an embodiment of the kit, wherein one catheter part is inserted for storage into another of the catheter parts thus substituting a catheter package.

FIG. 1 shows an embodiment of the catheter kit according to the present invention, wherein the first catheter section 20, not shown in FIG. 1, is sterilely packed inside the second catheter section 21, the second catheter section being sealed in both ends with sealing caps or foils 22,23.

Preferably the first section is coated with a hydrophilic coating, providing a low friction surface of the first catheter section when treated with a liquid swelling medium. The coating could be of the kind which sustains being activated with the liquid swelling medium for longer time, e.g. for several month. Thereby the liquid swelling medium could be provided in the catheter package from the time of packaging so as to provide a ready-to-use catheter. Hydrophilic coatings are known per se, see e.g. the published patent applications WO 98/58988, WO 98/58989, WO 98/58990 or EP 0570370. For this purpose, the sealing caps or foils should preferably be provided in a gas impermeable material for conservation of the humidity and thus the lubricity of the catheter for longer time, e.g. for several month. As an example, the second catheter section and/or the sealing caps may be made from a thermoplastic elatomeric material, other thermoplastic materials, curable elastomeric materials, polyamide resins or elastomers or any mixture thereof, i.e. the group may comprise materials like, PVC, PU, PE, latex, and/or Kraton™. The caps may be provided with a thickness allowing for sufficient gas impermeability. As an alternative, they may be made from metallised foils.

Figure 2:
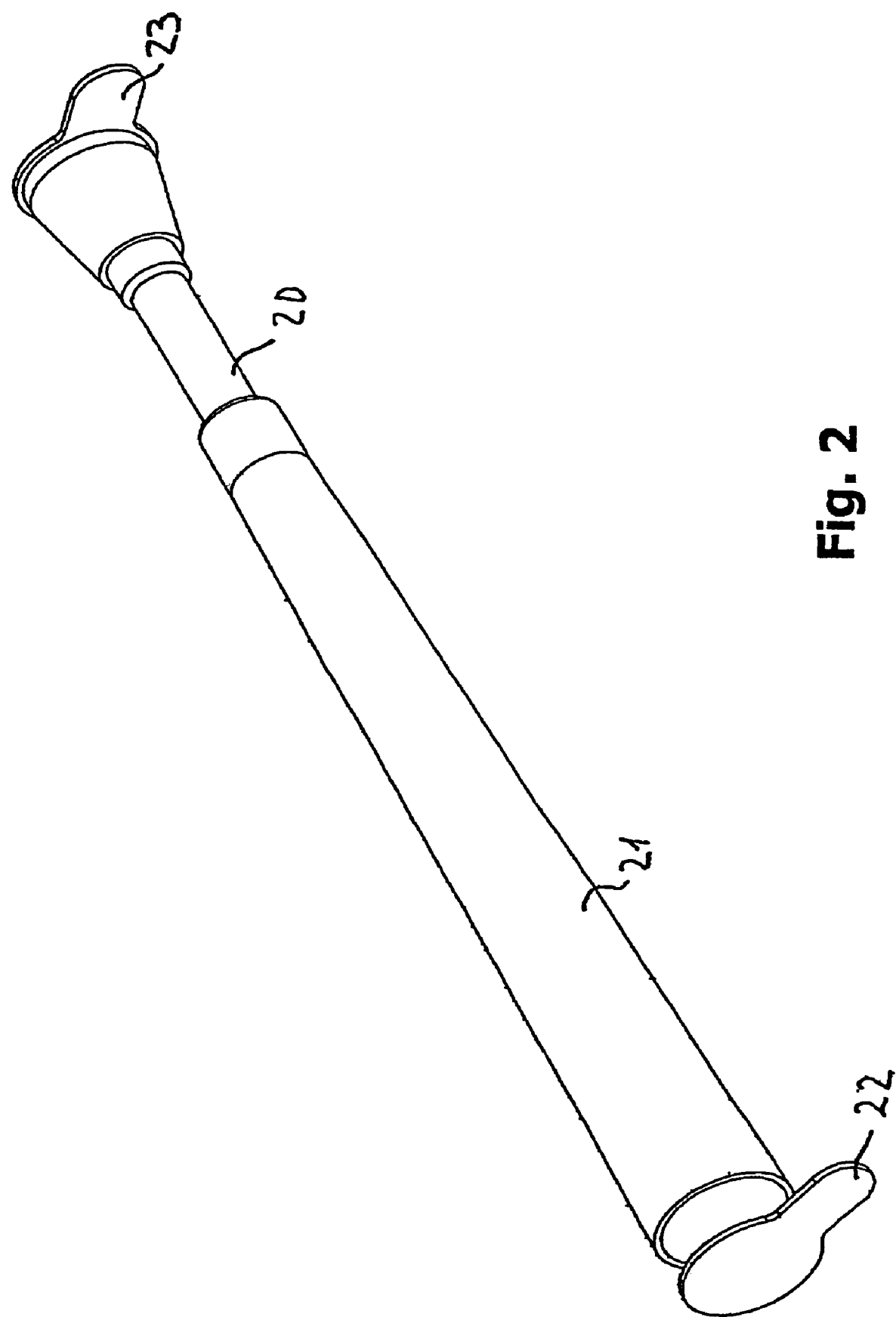
FIG. 2 shows the embodiment of FIG. 1, wherein the inserted catheter part is partially withdrawn from one end of the package.

As seen in FIG. 2, the first catheter section 20 is easily withdrawn from the second catheter section by pulling the cap or foil 23 which cap or foil engages the distal end of the first catheter section.

Figure 3:
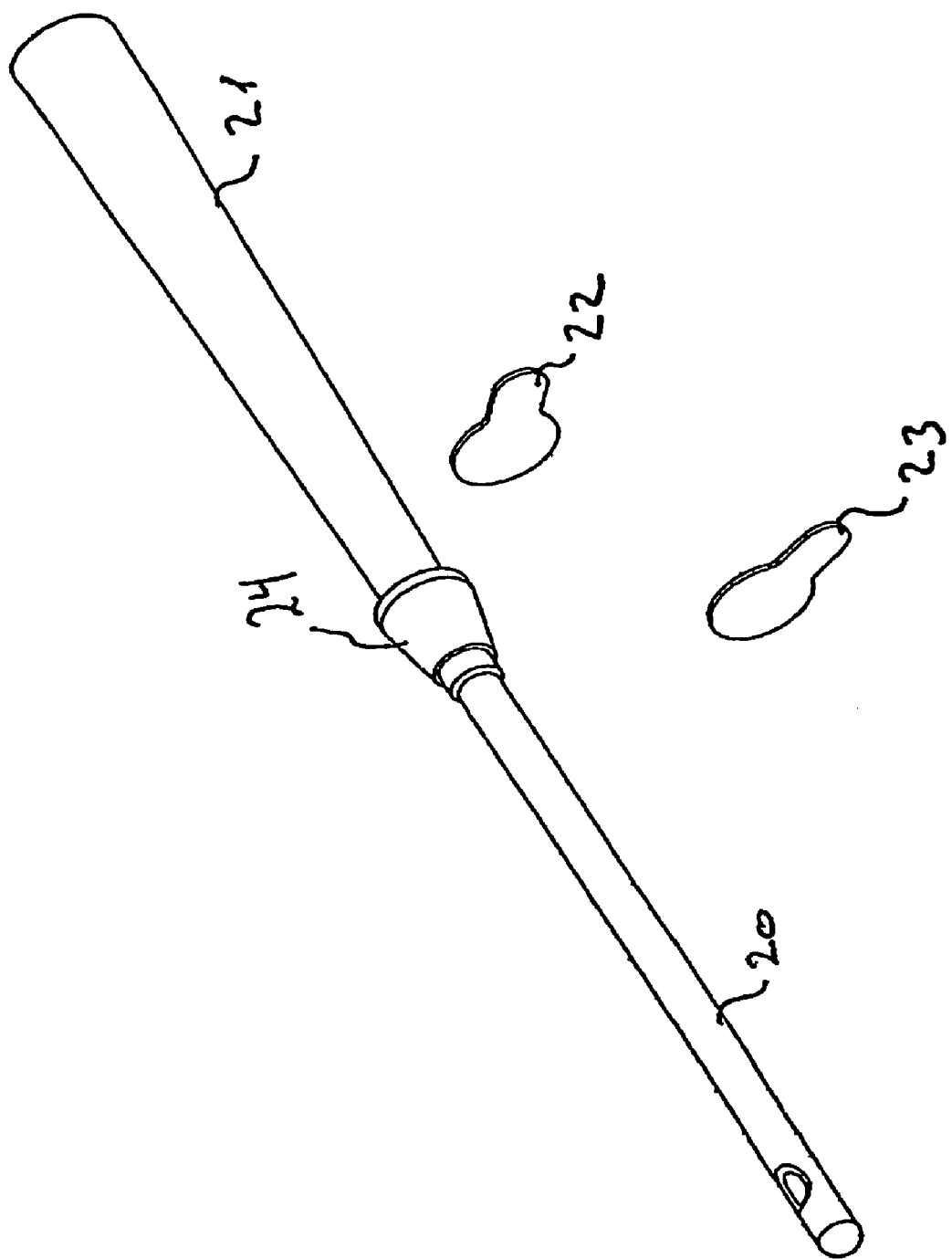
FIG. 3 shows the embodiment of FIGS. 1 and 2, wherein the inserted catheter part is completely withdrawn from the package and then attached to the other end of the package, the package thus functions as a handle for manipulation of the catheter.
Figure 4:
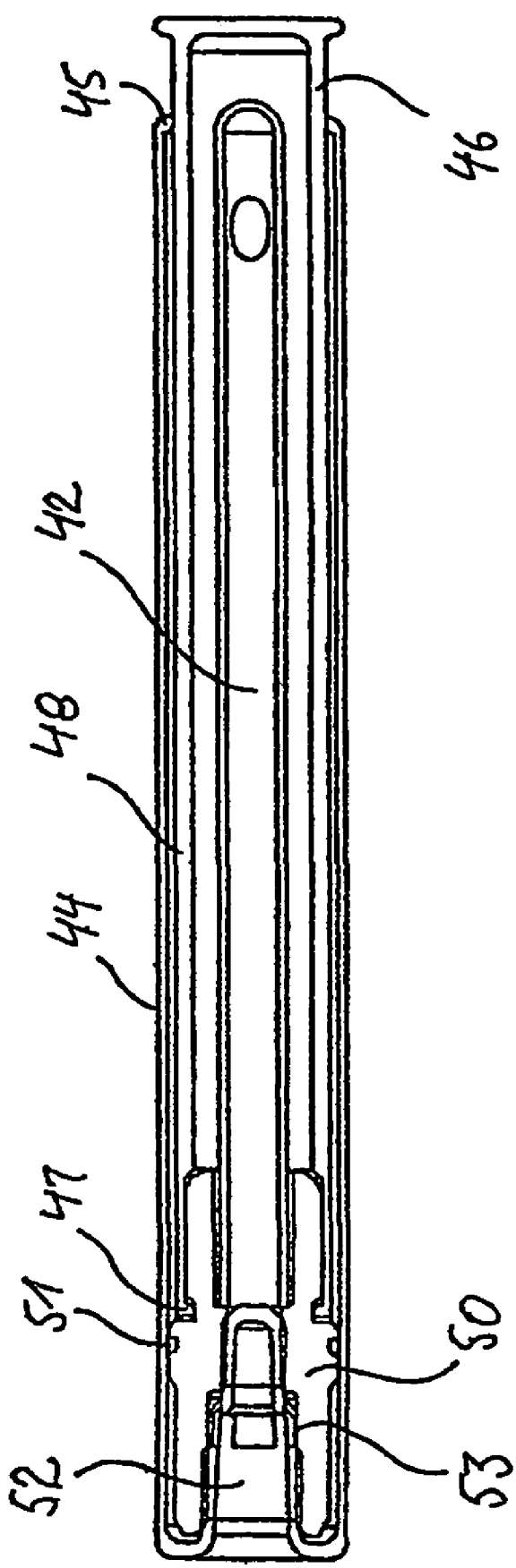
FIGS. 4-7 illustrate an embodiment of a kit according to the invention, wherein the catheter sections are arranged in a telescopic fashion.

FIG. 3 shows the assembled catheter after the first catheter section has been attached to the second catheter section. The foil or cap 23 can either be removed completely as shown in FIG. 9 or can at least be penetrated by the connecting means 24 of the second catheter section.

FIGS. 4-7 illustrate an embodiment of a catheter kit wherein the first and second sections 42, 44 are telescopically interconnected. A tubular protective member 46 surrounds a portion of the first catheter section 42 and forms a substantially annular cavity 48 around the first catheter section. In the second mutual configuration, shown in FIG. 4, in which the kit is intended to be stored and shipped, the first catheter section 42 and the tubular protective member 46 are inserted as far as possible into the second catheter section 44. A hydrophilic swelling medium, such as water, may be provided in the cavity 48, so that a hydrophilic surface coating optionally provided at the surface of the first catheter section 48 is stored in its swelled, i.e. wet condition. A surplus of hydrophilic swelling medium may be present in the cavity 48 in order to prevent the hydrophilic surface coating from drying out. A liquid-tight seal 50 is provided at the distal end of the first catheter section 42. A liquid-tight closing member 52 closes the distal end of the second catheter section 44. In one embodiment, the closing member 52 is removable so that a passage is provided between the second catheter section 44 and a urine collection bag, or another device for accumulating or conveying urine, mounted to the distal end of the section catheter section 44, when the closing member 52 is removed. In another embodiment, the closing member 52 is an integrated part of the second catheter section 44, in which case a wall 53 of the closing member 52 may be perforated in order to provide a passage between the second catheter section 44 and a urine collection bag, or other device for accumulating or conveying urine, mounted to the distal end of the section catheter section 44. In yet another embodiment, the closing member 52 may be substituted by a perforated end wall, e.g. a wall made from a central plate connected to the outer wall of the second catheter section 44 at its distal end by means of radially extending ribs or spokes. In such an embodiment, the first catheter section 42 and the seal 50 may be formed as a single, integrated piece.

Figure 5:
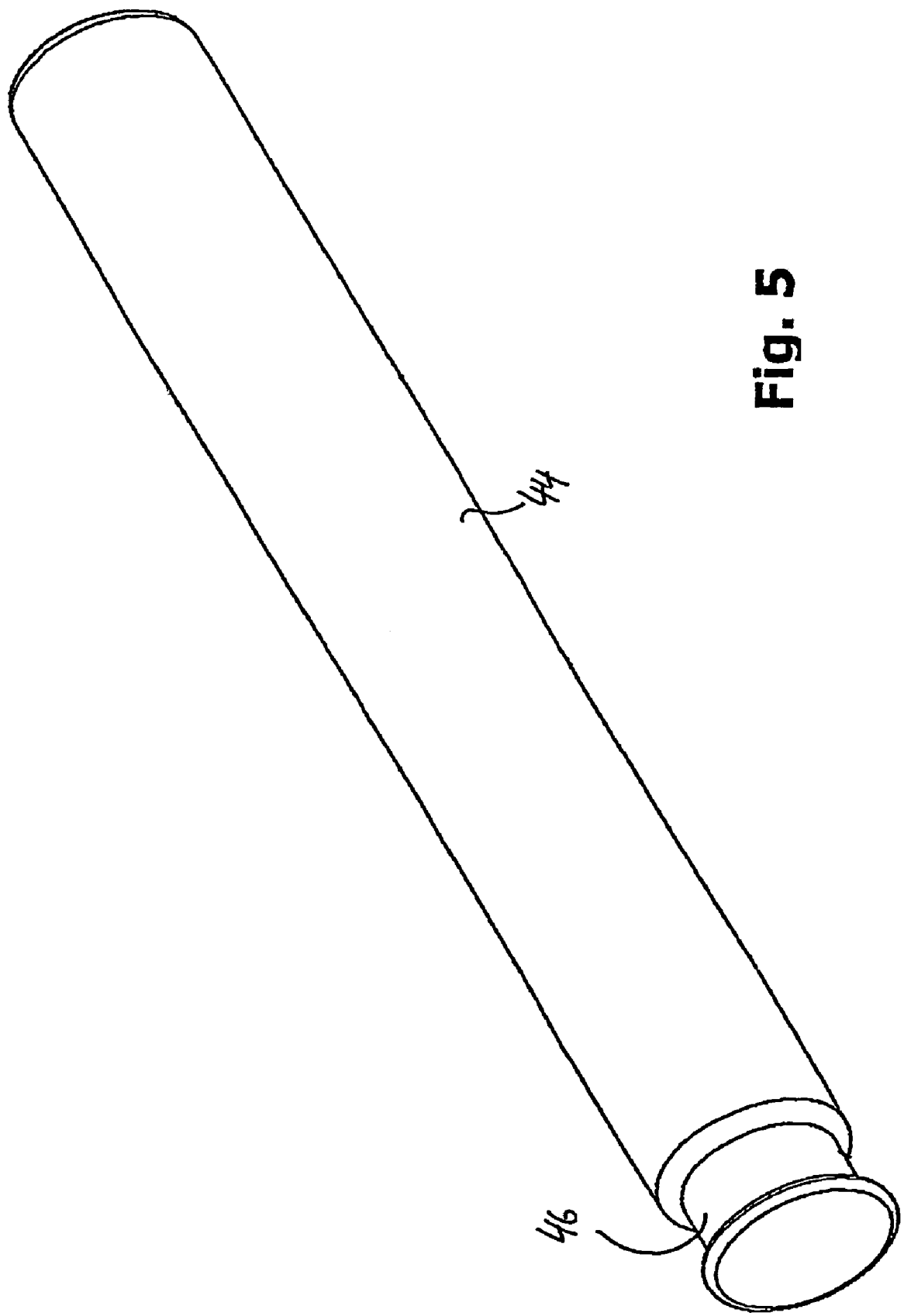
Figure 6:
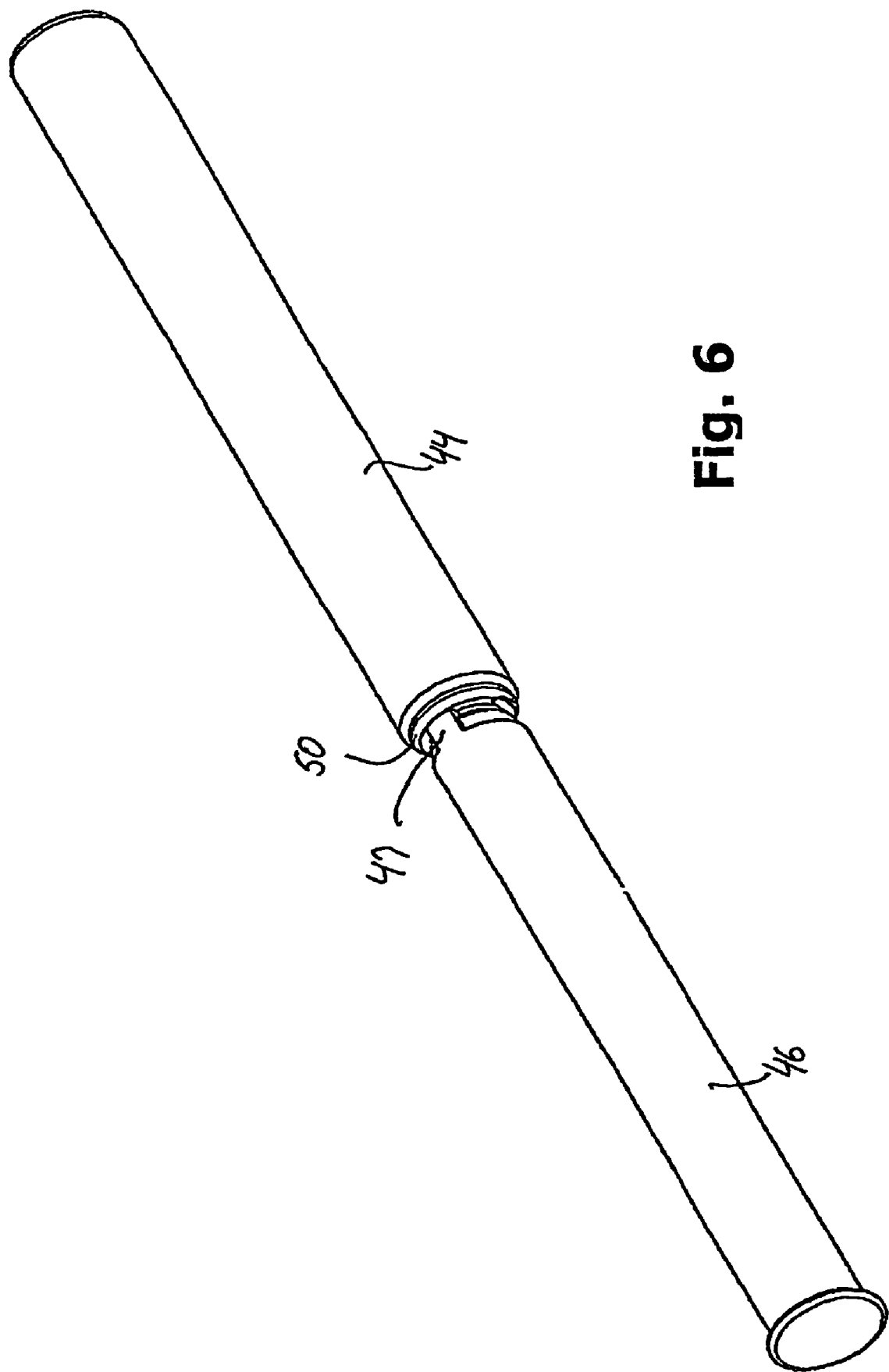
Figure 7:
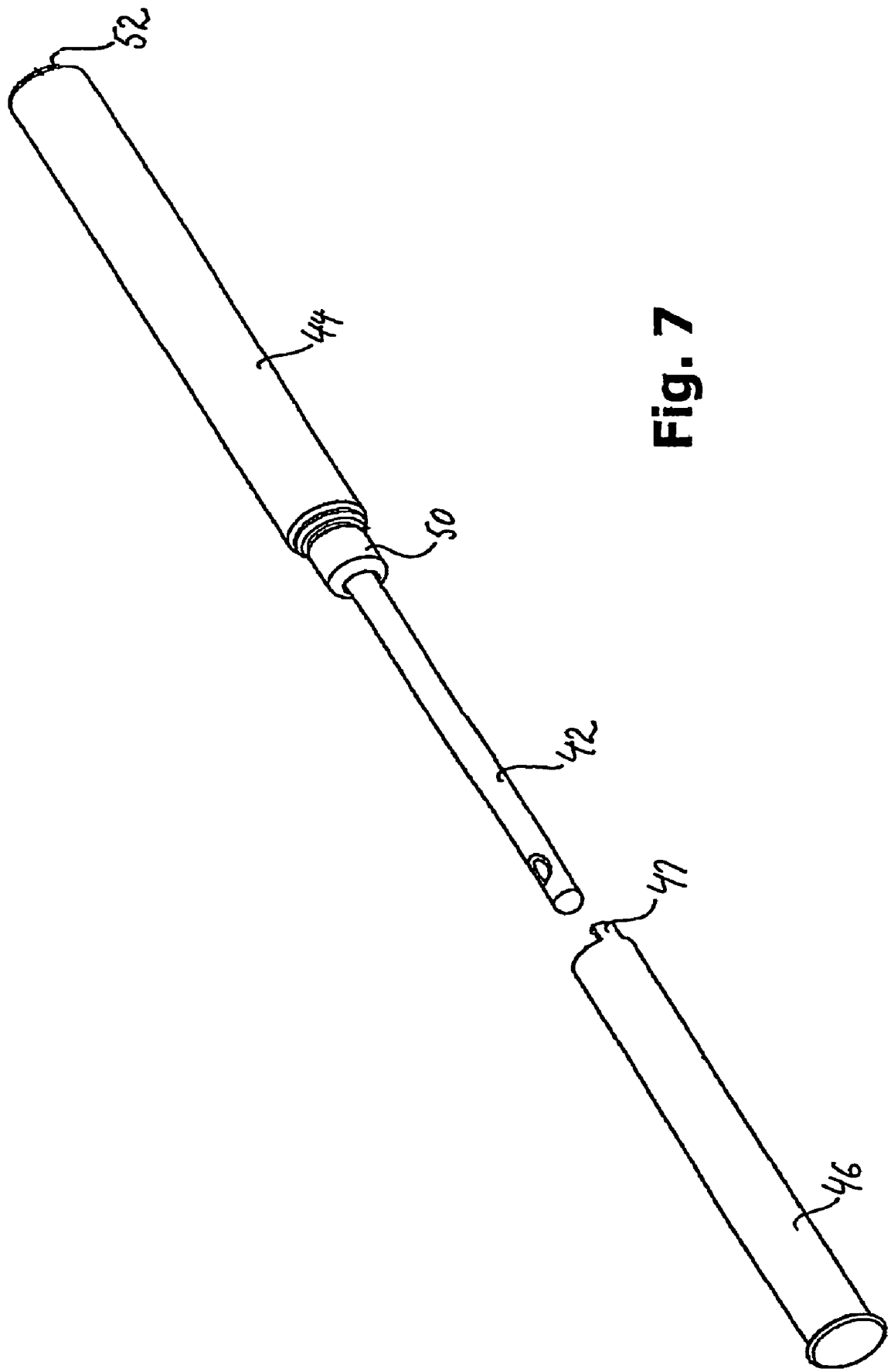
Figure 8:
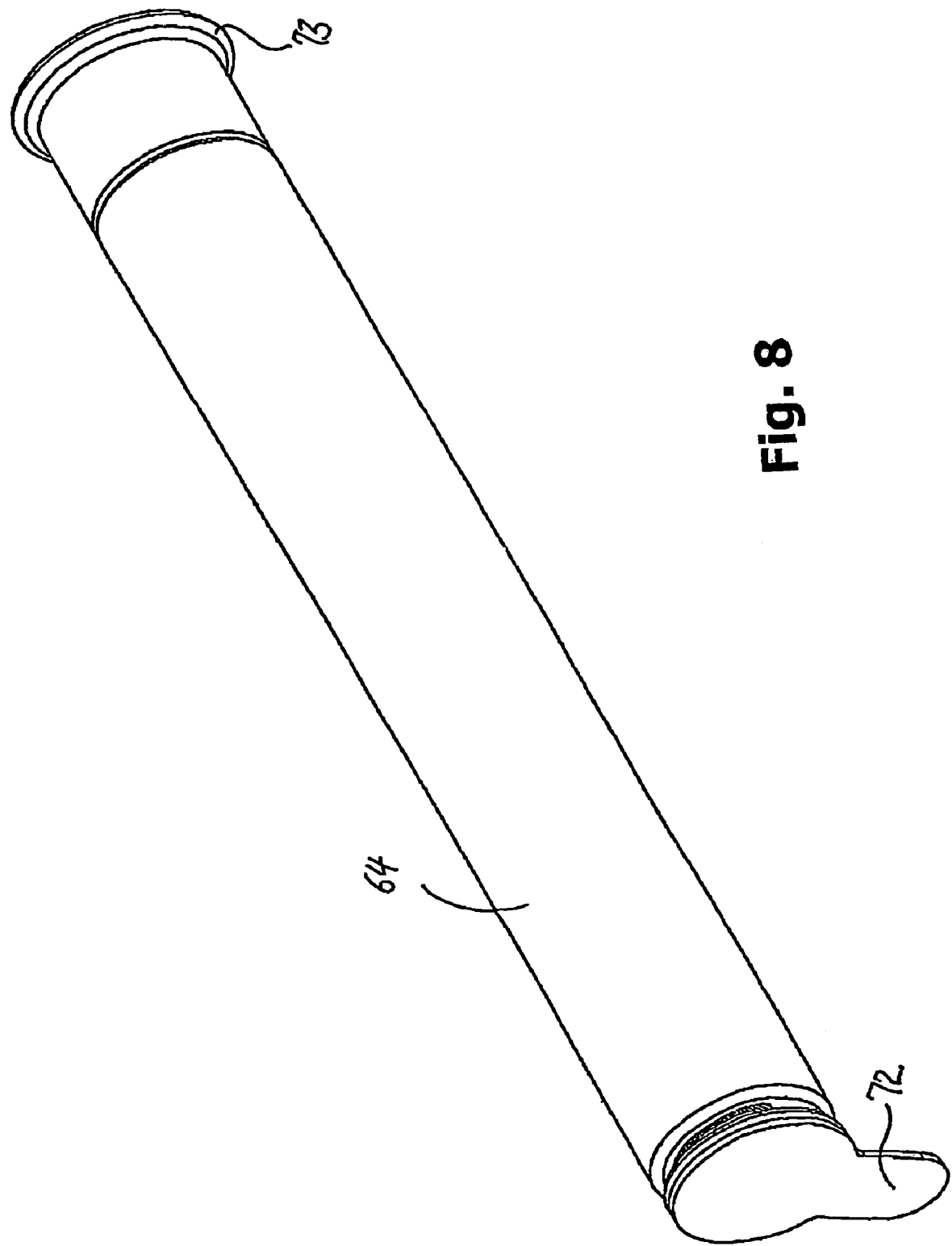
FIGS. 8-11 show a further embodiment, wherein the catheter sections are arranged in a telescopic fashion.

As shown in FIG. 5, an outer wall of the second catheter section 44 forms a handle, the tubular protective member 46 being arranged so that it extends out of the handle at the proximal end thereof. The tubular protective member 46 may form a flange at its proximal end, so as to facilitate a user's extraction of the first catheter section 42 and the tubular protective member 46 out of the handle/second catheter section 44. When extracted, the tubular protective member 46 and thus the first catheter section 42 surrounded thereby coextend with the handle or second catheter section 44, as illustrated in FIG. 6. A protrusion 47 at the distal end of the tubular protective member 46 releasably secures the tubular protective member 46 to the seal 50, see FIGS. 4, 6 and 7. The seal 50 may be designed so that it engages the proximal end portion of the second catheter section 44 by a snap action once the seal 50 and the tubular protective member 46 have reached the fully extracted position shown in FIG. 6. In the example shown in FIG. 4, the seal 50 has a groove 51 which, in the extracted position shown in FIGS. 6 and 7 engages a flange 45 at the proximal end of the second catheter section 44. Immediately prior to use of the catheter, the tubular protective member 46 is removed, so that the first catheter section 42 is exposed, as shown in FIG. 7.

Figure 9:
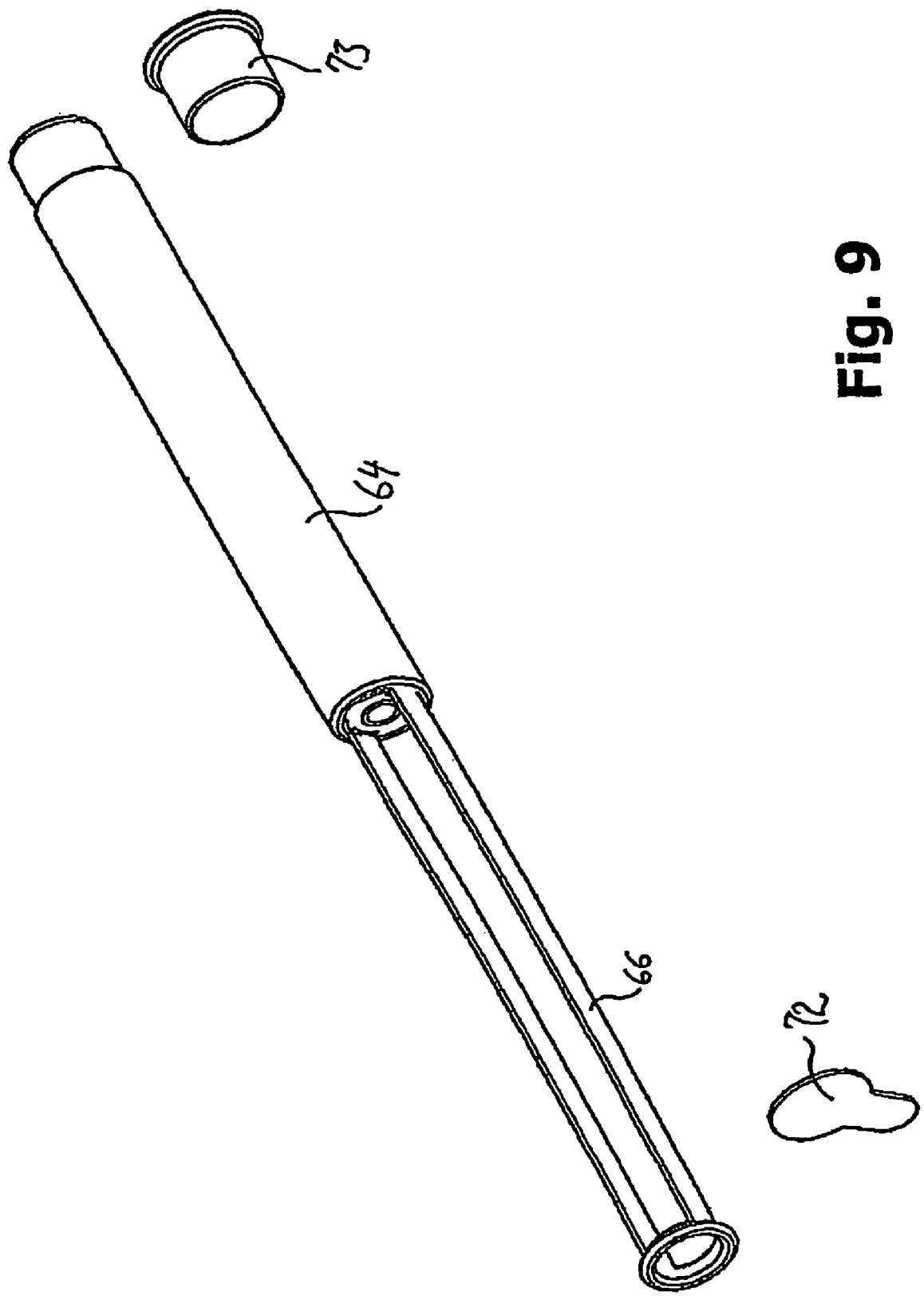
Figure 10:
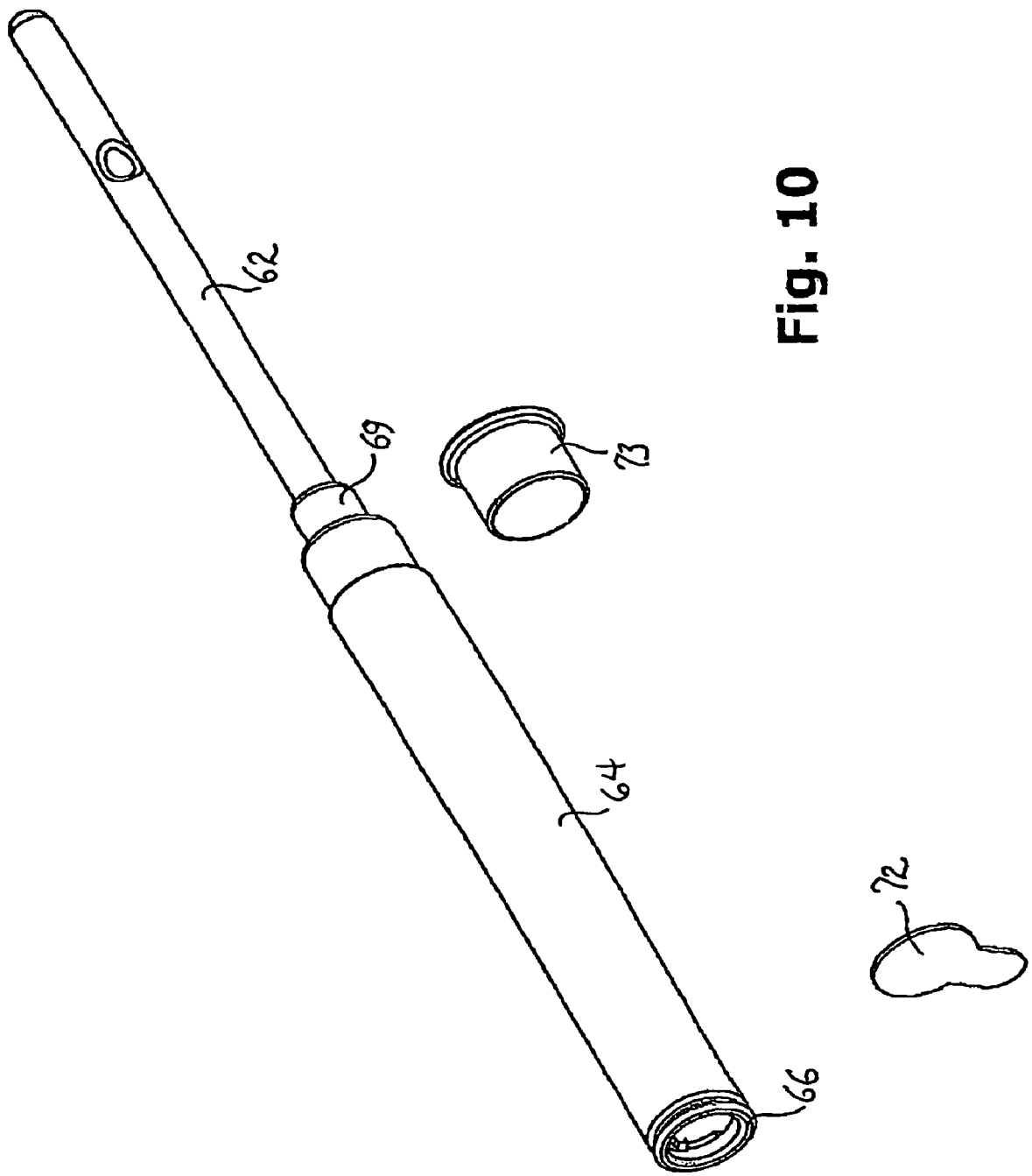
Figure 11:
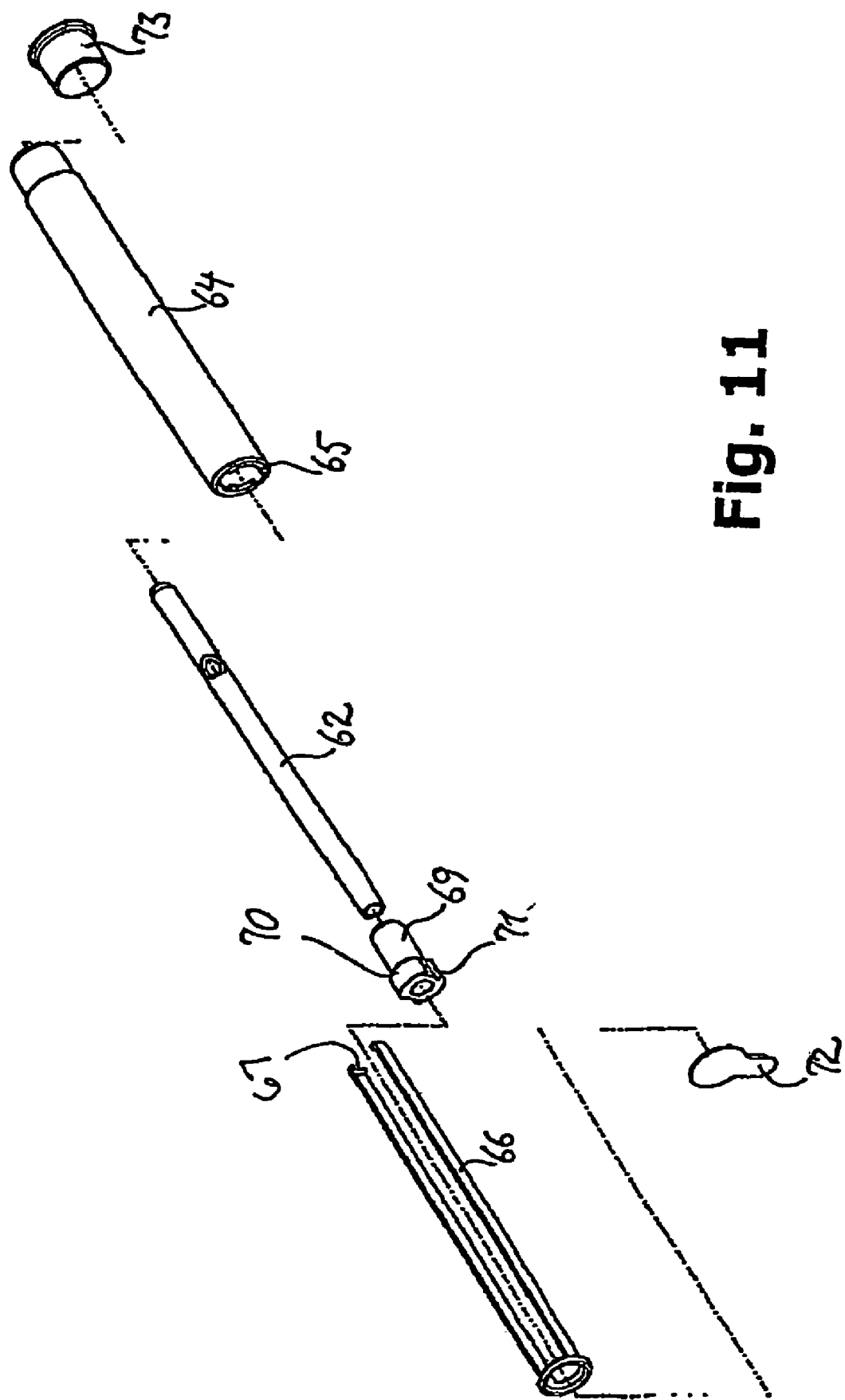

FIGS. 8-11 illustrate a further embodiment of a catheter kit, wherein the catheter sections are arranged in a telescopic fashion. As shown in the exploded view in FIG. 11, the kit comprises the following parts: a first catheter section 62, a second catheter section 64 with one or more inner flange portions 65, a guide member 66 with protrusions 67, a joint 69 with a collar portion 70 and slits 71 for the guide member 66, as well as a distal closure member 72 and a proximal closure member 73. The kit is stored and transported in the configuration shown in FIG. 8, wherein the second catheter section surrounds the first catheter section 62 and the guide member 66. Prior to use of the catheter, the distal closure member 72 is removed, and the guide member 66 is extracted, as shown in FIG. 9. The guide member 66 is extracted as far as possible, i.e. until the protrusions 67, due to their elasticity, engage respective grooves (not shown) provided in the slits 71 of the joint 69, see FIG. 11. The joint 69 is secured from sliding out of the second catheter section 64 by means of the inner flange portions 65 of the second catheter section 64. The proximal closure member 73 is also removed. Next, the guide member 66 is pushed back into the second catheter section 64. As the guide member engages the joint which is firmly connected to the distal end of the first catheter section, the joint 69 and the first catheter section 62 are pushed out of the distal end of the second catheter section 64 as the guide member 66 is pushed in the second catheter section 62. When the collar portion 70 of the joint 69 engages an inner flange or protrusion provided at the proximal end of the second catheter section 64, the kit is ready for use, and the first catheter section 62 may be introduced into the urethra of a human. A urine collection bag or other means for accumulating or conveying urine may be mounted to the proximal end of the second catheter section 64.

Figure 12:
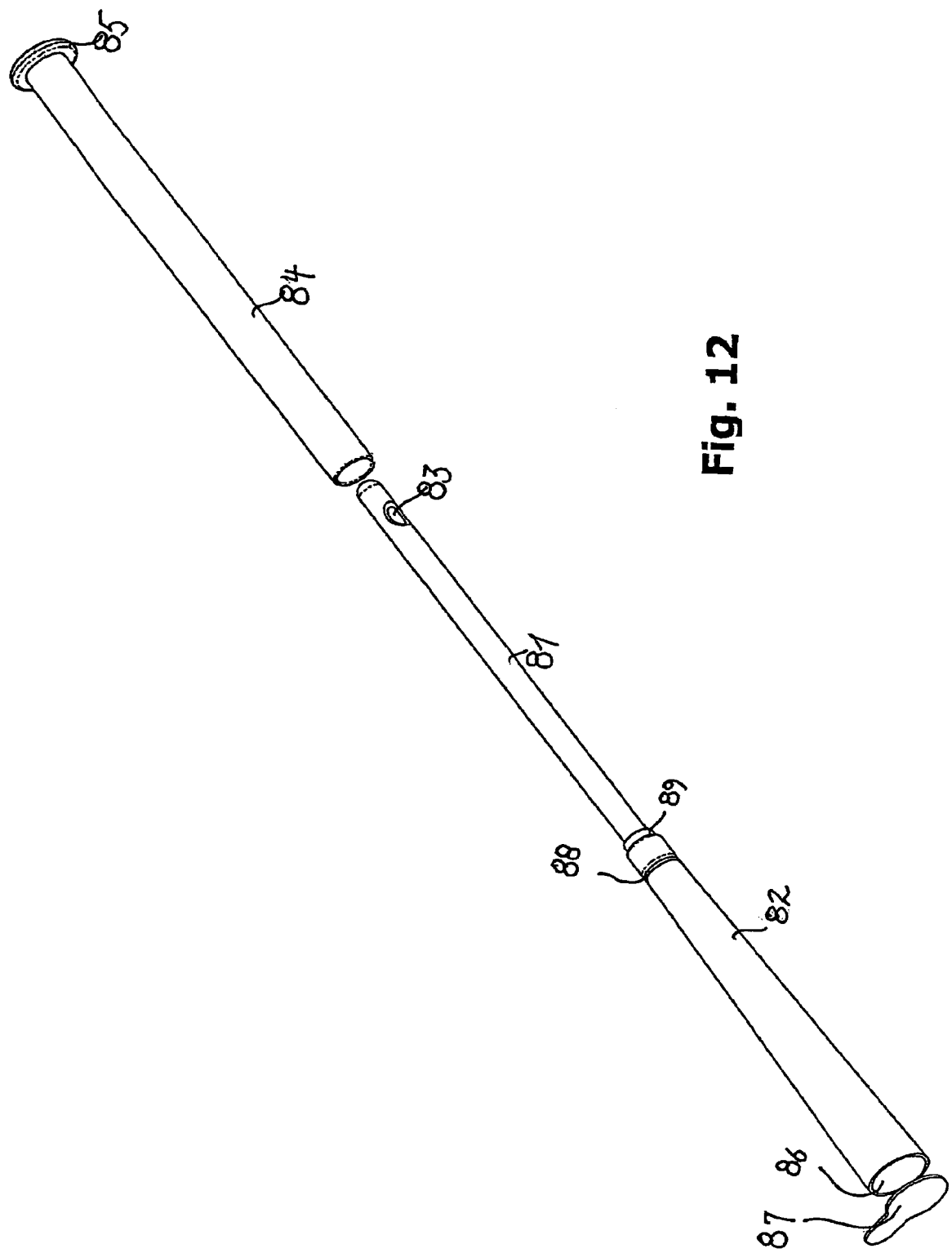

The catheter shown in FIG. 12 has a first section 81 forming the proximal, insertable end of the catheter, and a second, distal, section 82 forming a handle part of the catheter. The first and second sections may have different shapes corresponding to their intended use. The first section is oblong and has an inlet opening 83 for draining urine from the bladder into an internal conduit extending through both sections of the catheter, and the first section is slim when compared to the second part. The first section is covered by a tubular protective member 84 which is detachably attached to the outer surface of the catheter (in FIG. 12, the tubular protective member is removed and the catheter is ready for insertion into the urinary tract). The tubular protective member forms a substantially annular cavity around the first catheter section, having an open end that is removably connected to the second catheter section and a closed end distal from the open end so that, when the tubular protective member is connected to the second catheter section, both ends of the annular cavity are closed. The disclosed tubular protective member is cylindrical, and has an outward flange 85 supporting removal of the sleeve from the catheter. The internal conduit connects the inlet opening with the outlet opening 86 opposite the inlet opening in the second section. The outlet opening is covered by a foil 87 which is attached in a manner which allows peeling. A ribbed portion 88 gives the user a tactile indication of the transition between the first section and the second section. The first and second sections are joined in a joint 89, e.g. by gluing or welding. Alternatively, the sections may be made in one piece. As in the embodiment shown in FIGS. 4-7 discussed earlier, the substantially annular cavity around the first catheter section may be used for accommodating a friction-reducing substance so that the first catheter section is stored in a ready-to-use condition. Because both ends of the cavity are closed in the storage configuration, such friction-reducing substance is prevented from escaping through either one of the ends.

FIG. 13 shows the catheter of FIG. 12, wherein the tubular protective member 84 is attached to the catheter. The second section 82 is not covered by the tubular protective member in the storage configuration shown, i.e., the second section 82 is exposed to the ambient environment. The tubular protective member fastens to the second section via an inwardly extending flange (not shown) engaging the ribbed portion 88.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A urinary catheter kit comprising:
   a distal catheter section having an outlet at a distal end and a fastening mechanism disposed proximate to a proximal end;
   a lubricated proximal catheter section including an inlet proximate a proximal end and fixedly coupled with the distal catheter section so that a distal end of the proximal catheter section is coupled with the proximal end of the distal catheter section;
   a conduit forming a fluid passageway from the inlet to the outlet;
   a tubular member configured to enclose the lubricated proximal catheter section and including an attachment mechanism disposed at a distal end of the tubular member configured to releasably and sealingly engage the fastening mechanism to provide an enclosure around the lubricated proximal catheter section that is proximal to the fastening mechanism when the attachment mechanism is engaged with the fastening mechanism, wherein the fastening mechanism includes a rib disposed around a circumference of the distal catheter section.

2. The urinary catheter kit of claim 1, wherein the tubular member and the distal catheter section are positioned in an end to end relationship with one another when the attachment mechanism is engaged with the fastening mechanism.

3. The urinary catheter kit of claim 1, wherein a proximal end of the tubular member is positioned adjacent to the proximal end of the lubricated proximal catheter section when the attachment mechanism is engaged with the fastening mechanism.

4. The urinary catheter kit of claim 1, wherein the engagement of the fastening mechanism with the attachment mechanism provides a fluid tight seal.

5. The urinary catheter kit of claim 1, further comprising a liquid swelling medium disposed within the enclosure and the proximal catheter section includes a hydrophilic surface.

6. The urinary catheter kit of claim 1, further comprising an outward flange disposed on the proximal end of the tubular member.

7. A urinary catheter kit comprising:
   a distal catheter section having an outlet at a distal end and a fastening mechanism disposed proximate to a proximal end;
   a lubricated proximal catheter section including an inlet proximate a proximal end and fixedly coupled with the distal catheter section so that a distal end of the proximal catheter section is coupled with the proximal end of the distal catheter section;
   a conduit forming a fluid passageway from the inlet to the outlet; and
   a tubular member configured to enclose the lubricated proximal catheter section and including an attachment mechanism disposed at a distal end of the tubular member configured to releasably and sealingly engage the fastening mechanism to provide an enclosure around the lubricated proximal catheter section that is proximal to the fastening mechanism when the attachment mechanism is engaged with the fastening mechanism.

8. The urinary catheter kit of claim 7, wherein the cover is a foil member.

9. The urinary catheter kit of claim 1, wherein water is a lubricant for the lubricated proximal catheter section.

10. The urinary catheter kit of claim 1, wherein saline is a lubricant for the lubricated proximal catheter section.

11. The urinary catheter kit of claim 1, wherein a hydrogel is a lubricant for the lubricated proximal catheter section.

* * * * *